United States Patent [19]

Itil et al.

[11] Patent Number: 5,730,146
[45] Date of Patent: Mar. 24, 1998

[54] TRANSMITTING, ANALYZING AND REPORTING EEG DATA

[76] Inventors: Turan M. Itil; Emin Eralp; Pierre LeBars, all of 150 White Plains Rd., Tarrytown, N.Y. 10591

[21] Appl. No.: 194,125

[22] Filed: Feb. 9, 1994

Related U.S. Application Data

[63] Continuation of Ser. No. 739,254, Aug. 1, 1991, abandoned.

[51] Int. Cl.$^6$ ................................. A61B 5/0476
[52] U.S. Cl. ................. 128/732; 128/731; 128/630
[58] Field of Search ................. 128/903–906, 128/710, 709, 630, 731, 732, 920; 364/413.02

[56] References Cited

U.S. PATENT DOCUMENTS

| | | | |
|---|---|---|---|
| 3,724,455 | 4/1973 | Unger | 128/419 D |
| 3,810,102 | 5/1974 | Parks, III et al. | 364/413.02 |
| 3,886,314 | 5/1975 | Pori | 128/904 |
| 3,892,227 | 7/1975 | Coursin et al. | 128/731 |
| 4,407,299 | 10/1983 | Culver | 128/732 |
| 4,683,892 | 8/1987 | Johansson et al. | 128/731 |
| 4,744,029 | 5/1988 | Raviv et al. | 128/731 |
| 4,794,532 | 12/1988 | Leckband et al. | 364/413.06 |
| 4,838,275 | 6/1989 | Lee | 128/670 |
| 4,958,645 | 9/1990 | Cadell et al. | 128/903 |
| 5,012,411 | 4/1991 | Policastro et al. | 128/710 |
| 5,083,571 | 1/1992 | Prichep | 128/731 |

*Primary Examiner*—William E. Kamm
*Assistant Examiner*—Kennedy J. Schaetzle
*Attorney, Agent, or Firm*—Evelyn M. Sommer

[57] ABSTRACT

A method and system for acquisition, transmission, analysis, and analysis reporting of patient bioelectrical data, including electroencephalogram (EEG), computer-enhanced and expanded EEG (CEEG), dynamic brain mapping, evoked potentials (EP) and event related potential (ERP) data, with or without dynamic brain mapping, between a remote site where the physician and patient are located and a data collection and analysis center where the data can be analyzed by high-level computer analysis and/or expert technicians using an available communications channel. The EP, ERP and/or EEG data signals are gathered locally and transmitted using a local computer unit to control stimulus generation, data acquisition, and transmission functions. The high-level or computationally-intensive computer at the data collection and analysis center can also generate brain mapping analysis. The analysis results, along with statistical comparisons of the patient condition at the remote site with the data bases (normals, diagnostic groups, psychotropic drug data bases) at the receiving center are transmitted back over a communications channel to the remote site for display to the physician and patient.

10 Claims, 4 Drawing Sheets

TRANSMITTING, ANALYZING AND REPORTING EEG DATA

This application is a continuation of application Ser. No. 07/739,254, filed Aug. 1, 1991, now abandoned.

FIELD OF THE INVENTION

This invention generally relates to a method and system for transmitting, analyzing, and reporting on evoked potential (EP), event related potential (ERP), electroencephalogram (EEG) data, computer enhanced and expanded EEG (CEEG) data, and dynamic brain mapping data. In particular, the invention encompasses specially developed functions for gathering, transmitting, analyzing, and reporting on such data between a remote data gathering site and a data analysis center.

BACKGROUND ART

Digitization of analog brain electrical activity signals and quantitative analysis of the waveforms by computers are well known. Computers are also used for quantitative analysis (averaging) of evoked potentials (EP) and event related potentials (ERP) are used to determine the physiological responses of the brain to applied stimuli (somatosensory, auditory, visual, or more complex decide-and-react tasks) in order to evaluate brain dysfunctions. In recent years, the development of brain mapping techniques, as well as normative and clinical data bases, have made the above-mentioned technologies useful to practicing clinicians, particularly mental health care providers (psychiatrists, psychologists, social workers, etc.) who need to diagnose and treat disorders that may be related to brain function.

Such computerized systems require a sizable investment for the ordinary physician, as well as specific expertise in evaluating the results. A trained clinician is usually needed to make the appropriate clinical correlations.

It is well known to transmit electroencephalogram (EEG) signals via telephone from one location to another. The EEG signals are recorded and encoded by a transmitting unit, sent through conventional telephone lines by modulating the telephone carrier signal, and decoded at another site via a receiving unit. The receiving unit is connected to the input of a conventional EEG machine where the signals can be recorded on an analog strip chart and evaluated visually by a skilled technician. Telephonic EEG transmission systems have allowed untrained physicians to offer EEG services within their offices or clinics. However, the current telephonic EEG transmission systems are limited to basic visual analysis of EEG data evaluation, and are not able to perform sophisticated quantitative analysis, brain mapping, or EP and ERP response analysis services.

SUMMARY OF THE INVENTION

It is therefore a principal purpose of the invention to allow physicians to offer sophisticated diagnostic and treatment capabilities, such as computer analysis of EP and ERP responses, with or without brain mapping, as well as computer-analyzed EEG and dynamic brain mapping services, in their offices.

In accordance with the invention, a system for transmitting, analyzing, and reporting of patient bioelectrical (EP, ERP, or EEG) data comprises: a local computer at a remote site for controlling bioelectrical test administration, response data collection, and data transmission functions; signal gathering means located at the remote site, and operative in conjunction with said local computer, for creating and gathering signals indicative of the bioelectrical response of a patient at the remote site; data transmitting means located at the remote site, and operative in conjunction with said local computer, for transmitting data signals based upon the patient response signals to a data collection and analysis center at a different location from the remote site via an available communications link; data receiving means located at the data collection and analysis center for receiving the transmitted data signals from the remote site; data analysis means located at the data collection and analysis center for analyzing the received data signals and deriving an analysis result thereof; analysis transmitting means located at the data collection and analysis center for transmitting the analysis result back to the remote site; and analysis display means located at the remote site for receiving the transmitted analysis result and displaying it for the physician or patient.

In the system of the invention, an integrated combination of hardware, software, and bioelectrical activity measurement and analysis procedures is used for the recording and transmission of not only evoked potentials (EP) and event related potentials (ERP) but also electroencephalogram (EEG) data. The EP, ERP and/or EEG data are gathered at the remote site and transmitted by a special telephone modem or satellite transmitting unit to the data collection and analysis center over telephone lines or a satellite channel. High-level or computationally-intensive computer analyses of the brain activity data and brain mapping techniques are conducted at the data collection and analysis center (the receiving center), and the analysis results are transmitted back to the physician or caregiver at the remote site.

Using this invention, an untrained or unequipped physician can offer sophisticated EP, ERP, and EEG analysis, reporting, and diagnostic services in the doctor's office or in a hospital setting, without the need for a large investment in high-level computer and other equipment or specialized analysis training and personel. An enhanced range of brain activity states can be analyzed at the location of the patient, for example, the resting state (patient resting), sleep activated state (patient during all-night sleep or after sleep deprivation), after administration of a pharmacologic agent (patient is given an antiepileptic, hypnotic, anesthetic, analgesic, analeptic, or psychotropic drug and the brain's response is investigated within a few hours after drug administration to select the best available drug for each individual patient). An analysis can also be done after the administration of acoustic, visual or somatosensory stimuli and/or performance of a variety of tasks (evoked potentials or event related potentials).

Other objects, features, and advantages of the present invention will become apparent from the following detailed description of the best mode of practising the invention when considered in conjunction with following drawings.

DESCRIPTION OF THE PREFERRED EMBODIMENTS

The method and system of the present invention can be used for the transmission, analysis, and reporting on any type of bioelectrical signals obtained from a patient. For purposes of illustration, the following description describes an exemplary implementation of the system for EEG signals. A preferred form of EEG signal gathering instrument is disclosed in U.S. Pat. Nos. 4,632,122 and 4,683,892 issued to N. Johansson, E. Eralp, and T. Itil, U.S. Pat. No. 4,800,888 issued to T. Itil, D. Shapiro, E. Eralp, and N. Johansson, and U.S. application Ser. No. 07/388,210 of Akman et al., all of which are incorporated herein by reference.

Figure 1:
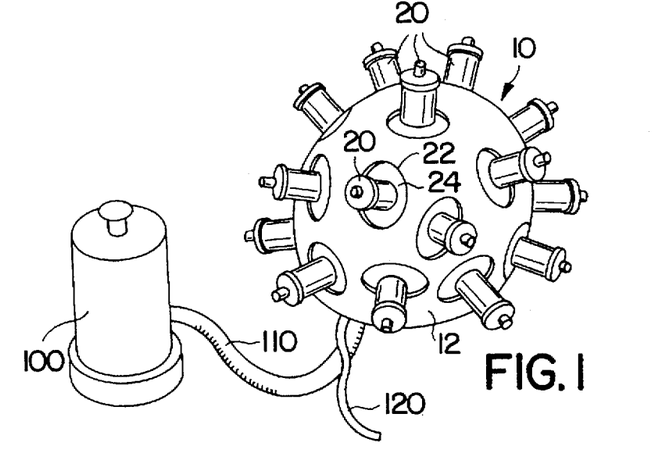
FIG. 1 is a diagram of a bioelectrical signal apparatus in the form of an EEG electrode headset for gathering EEG signals from a patient at a remote data gathering site.
Figure 2:
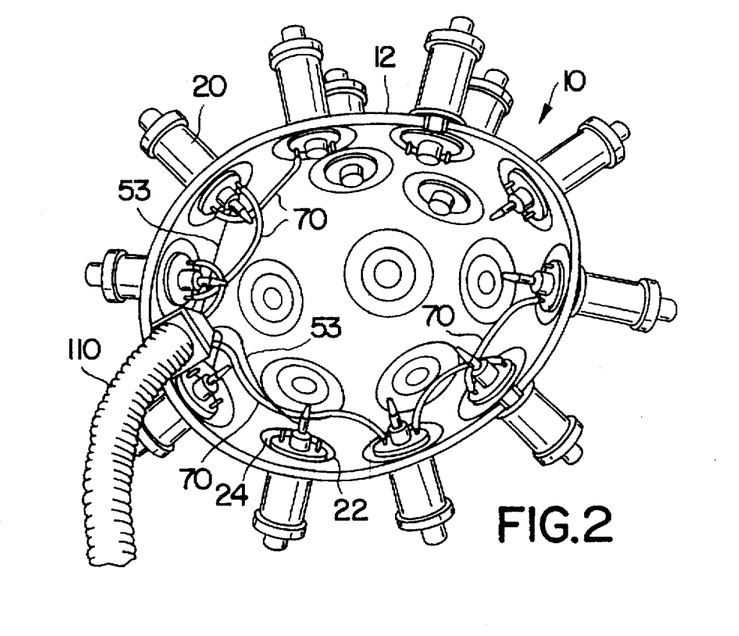
FIG. 2 is an internal view of the arrangement of the electrodes in the headset of FIG. 1.

As illustrated in FIGS. 1 and 2 herein, the EEG headset 10 of Johansson, Eralp, and Itil includes a helmet liner 12 with a plurality of electrodes 20 placed at predetermined positions about the liner 12. In order to accomodate each of the electrodes 20, apertures 22 are provided in the liner 12 and a resilient mesh 24 is used to hold the respective electrodes in position within the apertures 22. The mesh 24 permits ventilation of air through the liner 12, thus making the headset 10 more comfortable to wear, and its resilience allows the technician to oscillate the electrode tips to displace the subject's hair for placement in contact with the scalp. The electrodes 20 have respective tips 50 with ends that are to be placed in electrical contact with the scalp. Individual air-actuated cylinder and piston arrangements displace the respective electrode tips 50 against the scalp when air pressure is supplied through air conduits 70 fed by feed line 110 from an air pump 100. Conduits 53 are used to supply an electrolyte fluid or gel to the electrode tips 50 to ensure good electrical contact with the scalp. The electrolyte is supplied to the conduits 53 from a feed line 120 connected to an external electrolyte supply.

The EEG signal gathering system preferably incorporates signal conditioning hardware in the form of VLSI integrated unit for signal acquisition, amplification, conditioning, filtering, and output. A data transmission cable is attached to a D-connector coupled to the leads from the previously mentioned headset electrodes. An input selector is provided so that any combination or all of the 19 headset electrodes can be selected for input. Signal amplification controls are provided to amplify the signals for better signal-to-noise resolution. Signal conditioning circuitry is provided including an A/D converter, digital bandpass filter, and input reformatting circuitry. A data output module is configured, in accordance with the present invention, with telephone modulating circuitry enabling the system to perform as a telephonic transmission unit. The hardware system also has a user interface panel so that the appropriate electrode inputs, filter ranges, and amplification factors can be selected by the user. A CRT display may be used for display of selection parameters or the input signals for monitoring purposes. The hardware may also include a battery power supply for portability and patient safety. The hardware arrangement allows the headset system to be a complete bioelectrical signal gathering and recording system that is compact and self-contained. A black and white laser or color printer can provide hardcopies of the results analyzed in the receiver center and transmitted back to the physician's office.

Figure 3:
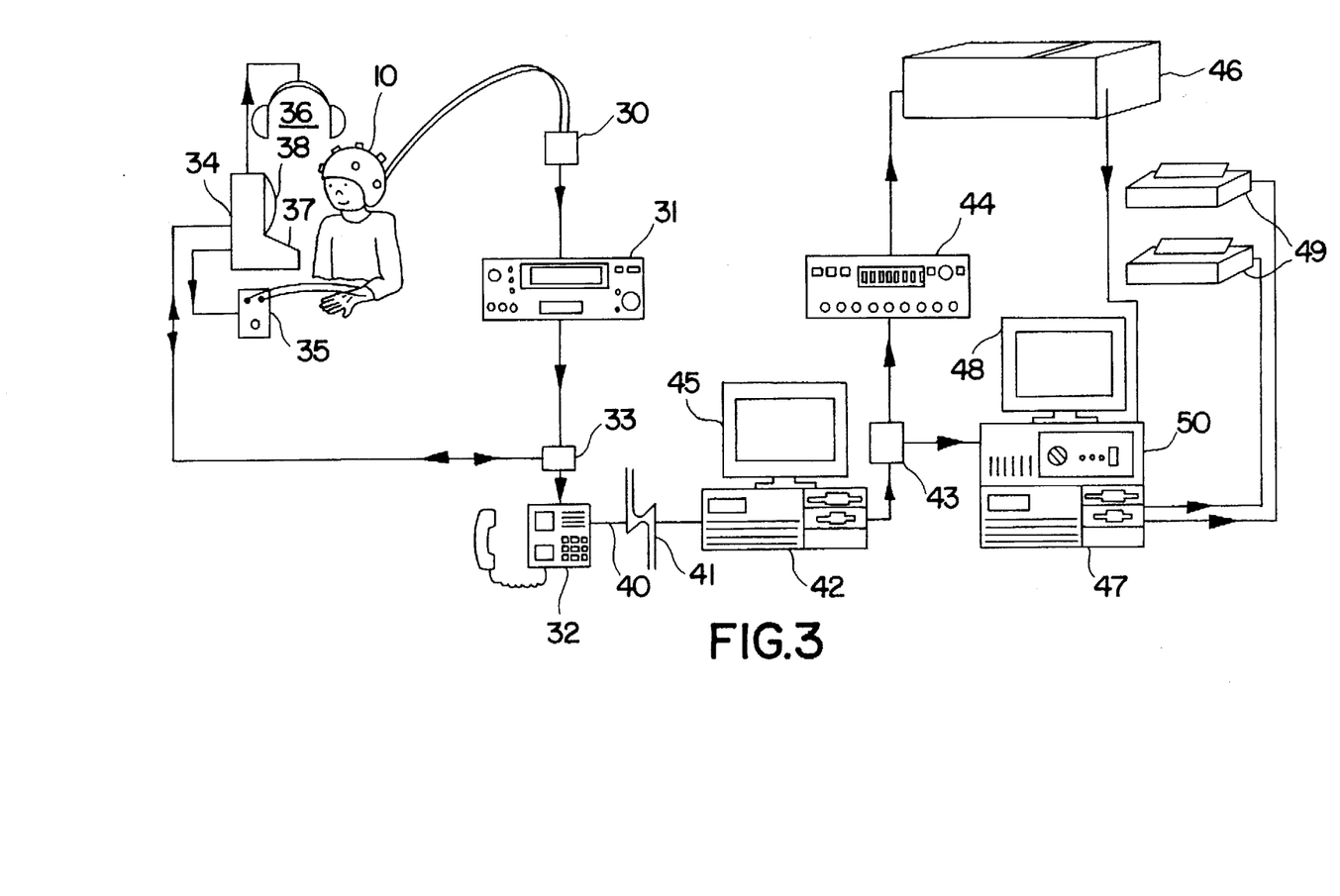
FIG. 3 is a schematic diagram of a data gathering, transmission, analyzing and reporting system for gathering, analyzing, and displaying bioelectrical data between a remote data gathering site and a data collection and analysis center in accordance with the invention.

Referring to FIG. 3, the bioelectrical data transmission, analysis, and reporting system of the invention is shown having the electrode headset 10 coupled via a D-connector 30 to a signal conditioning and transmitting unit 31 at a remote site where a patient is present. The signal conditioning and transmitting unit 31 is used to transmit data signals representing the bioelectrical signals obtained from the patient at the remote site to a data collection and analysis center in a location different than the remote site. The unit 31 is coupled to a local telephone line (or other communications link) 40 which is connected, through a telephone trunk line or satellite channel link 41, to a main control computer unit 42 at the data collection and analysis center.

A local computer unit 34 may also coupled to the transmitting unit 31 through a computer-controlled switching interface 33, so that the biolectrical data can be sent to the local computer unit 34 for digitization and display via a display screen 38 of the acquired data signals or analysis results locally at the remote site. The local computer may also be used for test administration functions such as generating acoustic stimuli provided to the patient through headphones 36, visual stimuli provided to the patient through the display screen 38, or somatosensory stimuli provided through a stimulus isolation unit 35 (for patient safety) for EP or ERP measurements. The user interacts with the local computer unit 34 using either the keyboard 37 or a mouse or other input device in order to select stimulation paradigms, data acquisition parameters, data display, or transmission protocols.

Figure 4:
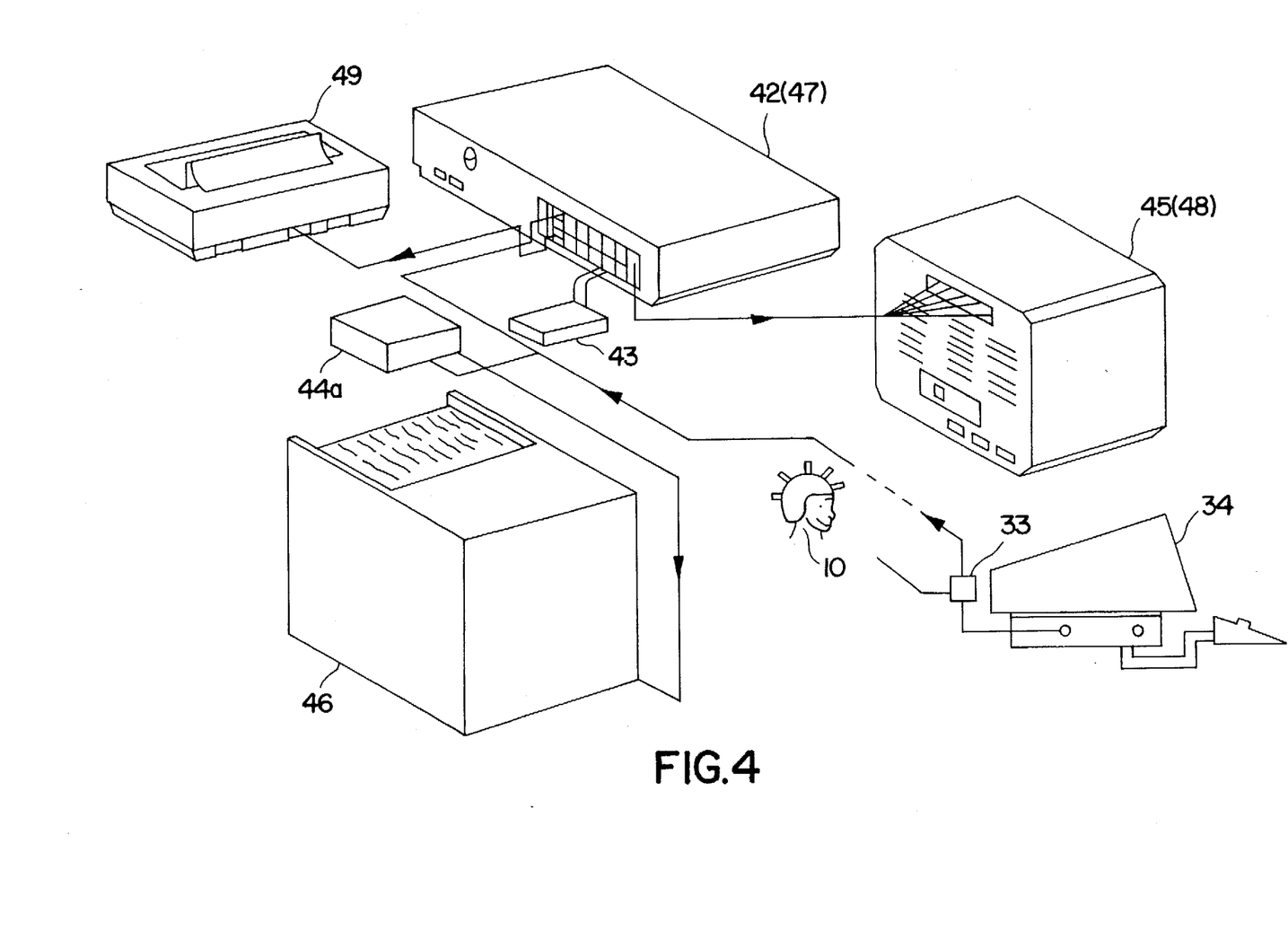
FIG. 4 is an illustration of another configuration of hardware components at the data collection and analysis center shown in FIG. 3.

FIG. 4 illustrates another configuration for the effective coupling of the electrode headset input and EP and ERP stimulator input from a remote site to the high-level analysis equipment at the data collection and analysis center. A main control computer 42 is connected to the communication link 41 via a high speed modem. The main control computer 42 receives the incoming data signals and routes them via a switch box 43 to a data receiving unit 44, which decodes the incoming signals and outputs them to an analog writer unit 46, and/or to the high-speed computer analysis equipment 47, which performs high-level quantitative analyses and/or brain mapping calculations based upon the received signals. The computational processing and analysis results can be displayed on a screen 48 for analysis by a trained technician, printed on printers 49, stored in the main control computer 42, and/or transmitted back to the remote site for viewing by the physician and/or patient.

A preferred implementation of the electrode signal conditioning and transmitting unit 31 has the following characteristics:

Frequency Response: 2–50 Hz.
Telephone Reqs.: Standard telephone line (–10 dbM line level).
Satellite Reqs.: Conforms to FCC satellite trans. criteria.
Total Distortion: Less than 5% through system telephone line.
Channel Intermod. Less than 5% at input 3× calibration voltage.
Calibration: Automatic internal calibration at 0.5 per second (10,25, 50, 100, 250, microvolts corresponding to gain control settings of 2, 5, 10, 20, 50)
Input Impedance: 4 Meg-ohms between differential inputs.
Comm. Mode Rej. Ratio: Greater than 80 db at 60 Hz. (10,000:1)
Preamp Noise Level: Less than 1 microvolt equivalent input.

The signal conditioning and transmitting unit 31 amplifies the brain electrical activity signals to increase the signal to noise ratio and then encodes them for transmission through standard telephone lines, or a satellite channel, or any other communications link. The common method of encoding EEG signals for telephone or satellite transmission is frequency modulation of a carrier signal. The first channel (1) of EEG data may modulate a 370 Hz. sine wave. For channel 1 to cover up to 70 Hz. (which is the desired frequency for EEG), the modulated signal will be 360+/−70 Hz. or 300–440 Hz. In addition to 140 Hz being used for transmission of the signal, it is standard practice to leave a 140 Hz. "guard band" to minimize crosstalk. The telephone transmission subsystem is capable of transmitting 10–20 channels of data using conventional phone lines, but fiber optic networks or satellite transmission systems can be used to increase the bandwidth of the existing channels and/or the number of channels up to 32.

Also included in the telephone transmission unit 31 is a preprogrammed transducer coupling selector so the electrical activity between a pair of transducers on the patient's head can be selected (which is common practice in EP, ERP, and EEG data recording). Since 10–20 channels are available (20-channel recording can be accomplished by cascading transmitters) for transmission, each selector position accommodates 8–16 pairs. The remaining 2–4 channels are used for transmitting control, timing and signal monitoring information from the local computer 34 for the EP and ERP stimulus generation and control subsystem (see below) and multiplexed digital information for use in generating brain mapping displays and statistical comparisons. The transmission unit includes voice communication capability for communication with the data collection center, and a signal button where the user can press a button to signal events for artifact control. Finally a timer is included so the user can time the procedure.

In order to record EEG during hyperalert, and/or cognitive activated states, and/or evoked or event related potentials, the patient must be given a stimulus or a cognitive event that will evoke a response in the brain. Most commonly used stimuli are visual, auditory (with or without cognitive components), and tactile (somatosensory). When acquiring evoked potential data it is imperative to know when the stimulus is given so that the brain's response to the stimulus can be measured precisely. In conventional EP systems an averager or a microcomputer with data acquisition capabilities is usually triggered to start data acquisition when the patient is stimulated. This presents a problem when an evoked potential is transmitted through the communications link. The stimulus signal is usually too short in duration. Because of the limited bandpass of the link, this signal will not be transmitted properly, thus a conventional EP system cannot be triggered to start data acquisition.

Other variants of conventional EP systems are ones that have the stimulators built in, and have a microprocessor that controls the stimulation by sending a trigger signal to the stimulator. In this case either it is impossible to separate the stimulators from the EP system so that the stimulators are at the remote site, and the data acquisition hardware is at the data analysis and collection site, or the control signals are again unsuitable for telephone transmission. Finally another problem that arises in the telephone or satellite transmission of EEGs and EPs is the acquisition of proper information about the stimulation parameters as well clinical information on the patient. No existing system is capable of transmitting the necessary recording and clinical information over telephone lines or through satellite systems or other communications links.

In order to overcome these problems, we have provided a microprocessor/software-based stimulator system 34 which properly stimulates the patient and transmits the essential triggering and time control signals to the data analysis and collection center for proper EP analysis. The specifications of an example of the stimulator system are as follows:

Processor: 32-bit internal, 16-bit external architechture.
Memory: 640 Kbytes
Graphics Res.: 640×480 monochrome
320×200 16-color
640×200 4-color
Color: Palette of 512 colors
Interfaces: RS-232 serial modem port
Parallel interface printer port
Floppy disk port (includes controller)
Monitor port
Mouse/joystick ports
Keyboard: 94-key intelligent keyboard using 6301 MPU
Power Supply: +5V @ 3A
+12V @ 1A
−12V @ 30 mA
Power Consumption: 95 Watts (maximum)

The stimulator system has three major functions. First, it is capable of generating a variety of audio, visual and somatosensory stimuli for EEG, ERP and EP recording. These are accurately synchronized with the brain function monitoring program operated at the data analysis and collection center. Second, the physician can record pertinent clinical information about the patient for transmission to the data analysis and collection center before the signal recording starts, so that the data analysis and collection center has all the necessary medical information about the patient. This computerized clinical information system also transmits all the necessary stimulus information to the data analysis and collection center. Third, a microprocessor can assist with digitizing the analog EEG data and, subsequently, either the analyzed or only the digitized data can be transmitted.

The software for the stimulator computer and display utilizes a series of pull-down menus to permit the user to quickly select any of several preconfigured ERP, EP or EEG sequences which have been designed to replicate some of the most clinically useful diagnostic paradigms. Each test begins with a description of the procedure followed by instructions to the patient. All user input is under mouse control so that minimal typing is required. The mouse is also used to control the experiment so that the user can pause, stop or change stimulus parameters. Finally, the system has an option where the user can prepare his/her own experimental paradigm which is then also transmitted to the data collection center. In the case of an EEG recording, the EEG signal is digitized and can be displayed on the CRT so that the user can monitor the signal. The primary analysis of the digital data is also done and transmitted to the data collection center to be used for statistical processing. This data is also correlated with the analog data received by the data collection center for artifact and signal control. The signals digitized at the data collection center and the transmitted digital signals are subtracted to further minimize phone transmission artifacts. In order to have the ability to generate all the necessary types of stimuli required for EEG, EP and ERP recording as well as having the necessary control and timing signals transmitted through standard communications links and have the capability of transmitting patient information, a flexible multipurpose microcomputer is necessary.

The audio, visual and somatosensory functions of the stimulator system were developed with the following specifications:

A. Visual Stimulator Component:

Repetition rate: 0.1 to 10 Hz in increments of 1/10 Hz.

Screen reversal: 14.28 msec.

Spatial frequency: 0 (flash)–50 Hz. (100×100 checks)

Presentation: Full/hemi field: left, right, top, bottom.

Fixation point: Carried through on all screens including a blank pause screen which initiates all tests.

Size of field: 5.125 inches, squared

Monitor image: High luminance, with no visible scan lines

Trigger advance: 42.84 to repetition period/2 in increments of 14.28 msec.

With these specifications, proper visual stimulation criteria are met and, because a fast refresh, high resolution screen is used, which is controlled by a microprocessor, faster screen reversals and screen building time, as well as greater selection of stimulus frequency, are obtained giving a more precise visual response.

B. Auditory Tone Burst Component:

Repetition rate: Continuous in increments of 14.28 msec.

Duration: Continuous increments of 14.29 msec.

Envelope (rise/fall): Fixed logarithmic, 5 msec.

Frequency: Continuous in increments of 0.048 microsec.

Memory: Up to 8 different tone frequencies in a programmable sequence of up to 500 steps Trigger advance: 25 msec. to repetition period in increments of 20 msec.

The auditory tone bursts are accomplished by a specially modified tone synthesizing component that is included within the system. It is able to generate the required range of auditory stimuli, and because it programmable, offers a much better dynamic range.

C. Click Component for Auditory Brain Stem Evoked Potential Recording:

Repetition rate: 1 to 35 Hz. in increments of 1/10 Hz.

Click risetime: 15 microsec.

Click falltime: 40 to 240 by 40 microseconds.

Stereo Output: Click in one ear, white noise in other.

D. Somatosensory Component:

Repetition rate: 0.1–35 Hz in increments of 1/10 Hz.

Pulse duration: 40 microsec.–1 msec., 40 microsec. incr.

Pulse delay: 25–100 msec. in 20 msec. incr.

Stimulus type: Constant current or constant voltage

The somatosensory component has been developed to drive an off-the-shelf stimulus isolation unit so that patient safety is maintained.

For signal monitoring and data acquisition for statistical analysis, the digital data are acquired and transmitted using an 8-channel high speed multiplexer, and a 1-channel A/D converter. The digital signals are then sent over the telephone line using a 9600-baud modem that is attached to the microcomputer, where they are analyzed and saved at the data collection center. The stimulator computer switches the telephone line from analog mode to digital transmission mode (for modem transmission) via a computerized switch. During EEG recording, as an option, the digital data can be displayed on the monitor 38 of the stimulator computer 34. The stimulator computer controls the data acquisition process and monitors the communications line. In case of communication line interruption, the digital data are saved, and streamed to the data collection center once communication or telephone contact is resumed.

The transmitted signals from the remote site is received at the data collection center through the main control computer 42 which monitors the incoming communications lines and routes the incoming signal either to the receiving unit 44 (in the case of analog signals) where an analog output is obtained and the signal is analyzed by the next available analysis station, or directly to the analysis station in the case of incoming digital signals.

The receiving unit 44 is part of the data collection center hardware and is connected directly to the main control computer via a software-controlled switch. Incoming analog signals are routed to the receiving unit 44. The specifications of a preferred implementation of the receiving unit are as follows:

Frequency Response: 1 to 50 Hz.

Signal to Noise Ratio: Better than 80:1, with 50 microvolts input calibration signal.

Wave Form Distortion: Less than 5% with input of 10 Hz., sine wave at 50 microvolts.

Power Requirements: 110 A.C. at 60 Hz. protected with 1/8 amp fuse.

Output Level: Adjustable from 0 to 200 microvolts.

Weight: 11 lbs.

Size: 5"×13.5"×9.5"

The incoming 10–32 channel analog signals are decoded by removing the carrier frequencies and outputting the signal to 10–32 separate lines. Each line contains a signal of each channel from the transmitting unit 31. Each of the lines can be put into the input of a conventional EEG machine and/or amplifiers to obtain the analog signal. Individual channel gain controls are available to calibrate each channel independently of the EEG machine and/or amplifiers. The technician is able to talk to the transmitting site directly through the receiving unit. In case the volume control on the transmitting unit is turned down, the receiving center can sound a tone to alert the user that the data collection center needs to talk to him.

The brain function monitoring subsystem operated at the data collection center is preferably a microcomputer-based electrophysiological data collection and analysis system integrated with microcomputer hardware and software. The hardware components of this subsystem are as follow:

A. Data Collection Microcomputer:

33 Mhz. 80386 microcomputer

33 Mhz. 80387 co-processor

130 Mbyte, 17 ms. hard disk drive 5.25" 1.2 Mbyte, and 3.5" 1.44 Mbyte floppy disk drives High resolution VGA compatible color board High resolution color monitor 2 parallel and 2 serial ports Enhanced keyboard 9600 baud high speed modem Although the above microcomputer configuration is currently used, any suitable equipment which will run the software can be used. The system can take advantage of subsequent improvements in hardware.

A special interface, indicated by the component 44a in FIG. 4, is used for interactive electrophysiological signal monitoring and filtering. Since the system was developed to be used with any off-the-shelf EEG machine, and/or amplifiers, and since these may have different signal conditioning specifications, the interface 44a was developed in order to standardize the acquired signal. A preferred implementation of the interface has 16–32 channel calibration signal generators that include 16 different frequencies for software checking and system calibration, and 16–32 channel bandpass filters at 24 db/octave in the bandpass of 1.3–50 Hz. used for anti-aliasing and baseline sway correction. An 11 Hz. 50 microvolt calibration output is used for calibrating the whole signal path of the system. Also employed is a 60 Hz. (50 Hz. for Europe), 36 db/octave notch filter for filtering line noise. A built-in bypass switch is provided for filtered or non-filtered recording (necessary for evoked potential recording). Software-controlled switching circuitry is used for software controlled switching between calibration and data acquisition modes. Software feedback circuitry checks for proper software control during data acquisition.

An analog to digital (A/D) converter unit 43 is used to convert the received analog signal to digital form for microcomputer processing. The analog to digital converter currently used has 12-bit resolution, and is capable of acquiring 1–16 channels under software control, with software-controllable variable gain (2.5, 5, 10 microvolts p-p). It is also capable of sampling up to 25,700 point/sec under software control. It has 16 digital I/O lines and 2 channels D-A, with external triggering capability under software control.

The data collection center uses a variety of output devices, including a black/white laser printer for text printout, and a high resolution ink-jet printer for color outputs. In this way all text outputs can be printed on the laser printer faster and more economically than using the color ink jet printer for all outputs. All printing is done under software control therefore universal printer drivers have been developed. With these drivers any kind of off-the-shelf printer, such as dot matrix or thermal printers or plotters, can be used with the system depending on the application.

Figure 5:
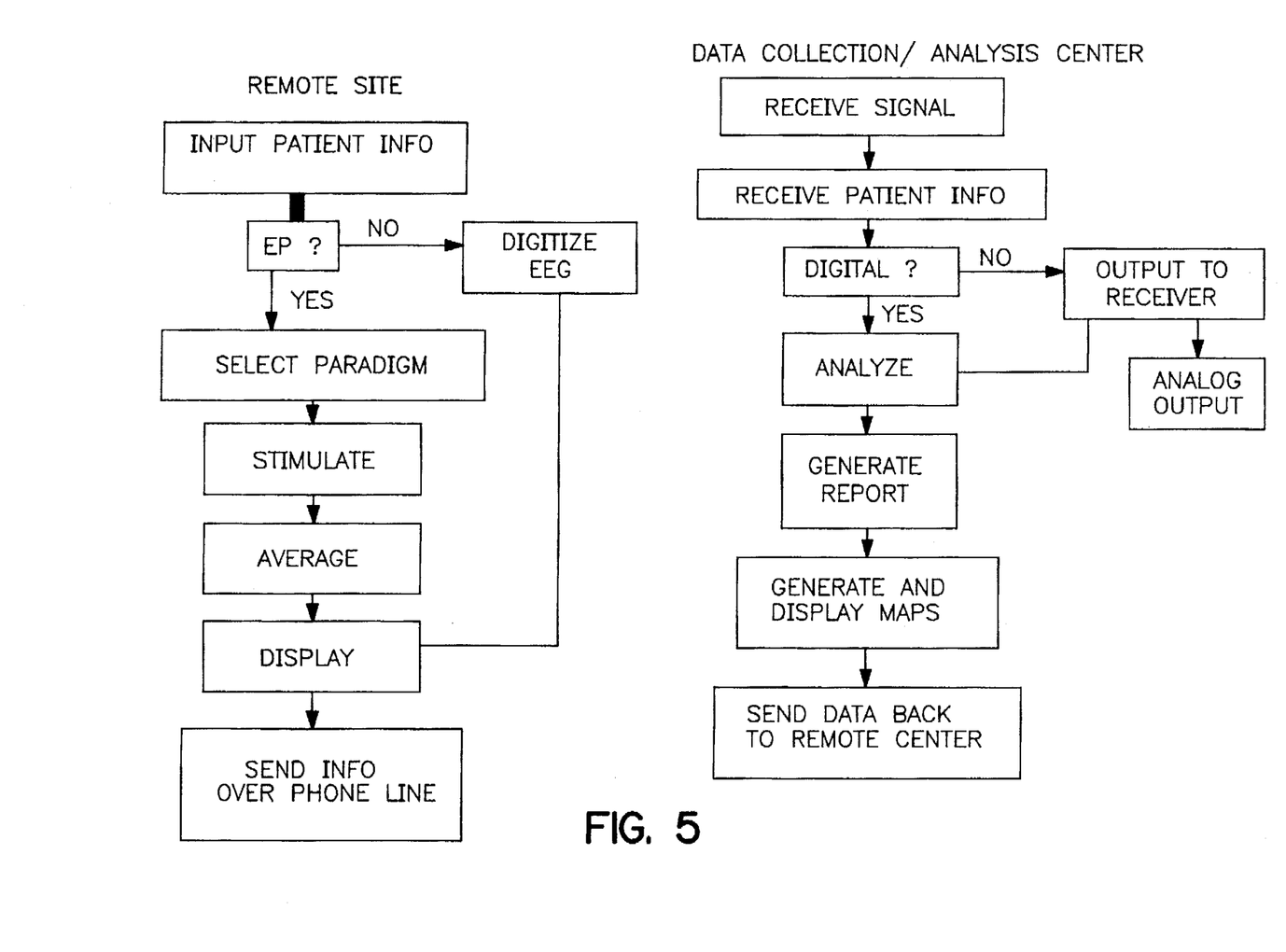
FIG. 5 is a block diagram of the complementary system functions executed between the remote data gathering site and the data analysis and collection center linked by a communications link.

The software for the data collection center includes the components described below and as illustrated by function blocks in FIG. 5. Patient information acquisition software is matched to the software at the data transmission site. When the computer 34 is used, an automatic data acquisition screen appears. The user is asked to enter the initials (name is not used to guarantee confidentiality of the patient), date of birth, sex, handedness, and social security number of the patient. Using the mouse, the user answers clinical questions necessary for the proper interpretation of the data to be obtained. When all the patient data has been entered, then the remote system enters the transmit mode. The automatic communications switch is switched so that the modem obtains a telephone line, and the data collection center is dialed. Once the data collection center is on line, the entered patient information is transmitted. Once the transmission is completed, the switch is switched so that the electrophysical data transmission subsystem is on line. The same procedures can be applied if satellite transmission is used.

If the user has requested an EP or ERP analysis, then the computer 34 displays the EP recording protocol list on the screen. With the mouse the user selects the appropriate stimulation protocol and prepares the patient. Once the stimulation is started then instructions to the patient appear on the screen and pressing the mouse initiates the testing. During the testing a trigger signal for each testing sweep and stimulation control information are sent on different channels though the communications link. During the EP or ERP testing the system can be paused and resumed at any time by pressing the appropriate mouse buttons.

At the data collection center, the software to control and acquire the electrophysiological data is installed. The software switches the communications link to the receiving modem, and the software is in the answer mode. When a remote site calls in, the telephone is automatically answered, and the patient information is collected. Once all patient data has been received, the system switches the communications link to receive EP, ERP, or EEG data and the software performs a calibration. This is done by switching the interface 44a into a calibration mode, and acquiring the calibration signal. The results of the calibration are displayed on the monitor 45 where the recording technician can check the signal integrity and decide whether to commence or to restart the procedure.

Once the technician signals that the calibration is acceptable, then the software switches the interface into data acquisition mode, and the system is ready to acquire the incoming electrophysiological data. The technician then signals the beginning of the recording to the transmitting site, and the center executes the predetermined protocol for recording. If the test is an EEG, the resultant signal is sent to the data recorder 46 (which can be an EEG machine or amplifiers with an analog writer unit attached) and an analog paper record is generated. During the recording the digital signal is also displayed on the monitor, and maps for every 5 seconds are also displayed. At all times, built-in automatic artifact detection and rejection routines monitor the signal, and the recording technician can also reject samples that are deemed to be artifacts by pressing a button on the keyboard. At the end of the recording, the automatic printing routines generate a report and the necessary brain maps and norm comparisons needed for the recording.

If the incoming test is an EP (or ERP), then the system alerts the technician to switch the interface into EP mode, and the software enters an EP data acquisition mode. For EP data acquisition, the calibration signal sent from the transmitting site is acquired and used for automatic d.c. correction and digital value to microvolt conversion correction. The system is then put in EP data acquisition mode, and waits until the transmitting site starts the EP stimulation. During the recording, the software acquires a sweep every time a trigger is sent, and the stimulus timing information is acquired. During the recording of the EP (or ERP) data, the resultant average, as well as the single sweeps, are displayed on the monitor for signal control, and the automatic artifacting routines monitor the signal for artifacts. If an artifact is encountered the sweep is rejected. The technician can also manually reject sweeps by pressing a button. After the EP data collection, the automatic peak finding routines label the appropriate peaks in the average. These are checked by the technician, who can also correct for d.c. drift and filter the signal.

Once the integrity of all the acquired EP data has been checked, then the automatic printing routines print the report, the averages with pertinent peaks labeled, the norm comparisons, and the necessary maps. The analysis results and brain maps are also transmitted back to the remote site for display to the physician and/or patient. The receiving unit 42 includes a secondary transmitter portion for sending, and the transmitting unit 31 includes a secondary receiver for receiving, the transmitted analysis results from the data collection and analysis center and transferring them to the computer 34 for display on the monitor screen 38, as well as hard copy black and white reports, color brain maps, and histograms.

The above-described hardware, software and procedural components offer the following advantages over conventional telephone EEG transmission systems. The system includes the transmission of evoked potential (EP) and event related potential (ERP) data, with or without dynamic brain mapping, and computer analysis of the electroencephalogram where the data are provided with objective digital numbers. Because of the availability of the objective data, one can obtain dynamic brain mapping according to frequency distribution or other parameters, statistical comparisons for the objective differential diagnosis of patients against data base groups, and brain electrical activity information from thousands of interpolated areas in addition to the 16-32 real recorded areas. Thus one can develop many different types of brain mappings. If, in a particular area, no telephone lines are available, or they are not clear enough, alternate communications links (e.g., satellite systems) can be used.

The quantitative EEG data collection and analysis allow physicians to obtain not only EEG and EP reports prepared according to American EEG Society standards, but also brain maps, norm comparisons, diagnostic group comparisons, statistical histograms, and drug data base comparisons. This information, which is not available with conventional EEG, transforms the subjective method of EEG to an objective/scientific medical tool which is helpful in the diagnosis and treatment of disorders related to brain dysfunction.

Numerous modifications and variations are of course possible in light of the principles of the invention disclosed above. It is intended that all such modifications and variations be included within the spirit and scope of the invention, as particularly defined in the following claims.

We claim:

1. A system for transmitting, analyzing, and reporting of patient bioelectrical data for a physician attending a patient at a remote site, comprising:

a local computer at the remote site for controlling the administration of a local bioelectrical test to the patient by the physician, the collection of response data generated from the administered test, and the transmission of response data to a data collection and analysis center;

signal gathering means located at the remote site, and operative in conjunction with said local computer, for gathering signals indicative of the bioelectrical response of the patient to the test administered at the remote site;

first telephonic transmitting/receiving means located at the remote site, and operative in conjunction with said local computer, for establishing a high-speed, multi-channel telephonic communications link with, and transmitting response data based upon the patient response signals to, a data collection and analysis center at a distant and different location from the remote site concurrently with the administration of the test;

second telephonic transmitting/receiving means located at the distant data collection and analysis center for receiving the transmitted response data signals from the remote site and for transmitting the analysis results back to the remote site;

computerized data analysis means located at the data collection and analysis center for analyzing the received data signals, deriving analysis results therefrom, and transmitting the analysis results back to the remote site via said telephonic communications link between said first and second telephonic transmitting/receiving means; and display means located at the remote site, and operative in conjunction with said local computer, for receiving the transmitted analysis results and displaying it to the physician or patient concurrently with the administration of the test.

2. A system according to claim 1, wherein said signal gathering means includes a headset having a plurality of electrodes mounted therein for taking EP, ERP or EEG measurements of brain activity signals at a plurality of points on the head of the patient.

3. A system according to claim 2, wherein said computerized data analysis means includes brain mapping program means for analyzing the brain activity signals transmitted from the remote site and returning a brain mapping result for concurrent display of the patient's brain activity at the remote site.

4. A system according to claim 1, wherein said first and second transmitting/receiving means are telephonic data and voice, modems which allow a voice communications link to be established between the physician and a clinician at said data collection and analysis center concurrently with transmission of the response data signals and analysis results between the remote site and the data collection and analysis center.

5. A system according to claim 1, wherein said local computer at the remote site is coupled to a peripheral instrument for concurrently measuring and transmitting to the data collection and analysis center other physiological data signals measured from the patient, and said computerized data analysis means includes analysis program means for analyzing the physiological data signals and factoring them into the analysis results.

6. A system according to claim 1, wherein said local computer is coupled to headphones and a stimulator isolation unit for generating a plurality of different types of patient stimulus signals, and said local computer includes stimulus program means for controlling the administration of the different types of patient stimulus signals to the patient for producing an evoked potential or an event related potential response from the patient.

7. A system according to claim 6, wherein said local computer and stimulus program means control the administration of visual stimuli on said display means, auditory sounds on said headphones, and somatosensory stimuli through said stimulator isolation unit.

8. A system according to claim 1, wherein said computerized data analysis means includes patient information acquisition program means for acquiring and analyzing patient information in conjunction with analyzing the response data signals gathered from the patient at the remote site.

9. A system according to claim 1, wherein said computerized data analysis means includes evoked potential (EP) and event related potential (ERP) analysis program means for analyzing EP and ERP response data gathered at the remote site.

10. A system according to claim 1, wherein said computerized data analysis means includes artifact rejection program means for rejecting spurious artifact signals received with the response data transmitted from the remote site.

* * * * *